United States Patent
Bohn et al.

(12) 
(10) Patent No.: US 6,352,686 B2
(45) Date of Patent: *Mar. 5, 2002

(54) ANTIPSORIATIC NAIL POLISH

(75) Inventors: Manfred Bohn, Hofheim; Karl Theodor Kraemer, Langen, both of (DE)

(73) Assignee: Aventis Pharma Deutschland GmbH, Frankfurt am Main (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/135,657

(22) Filed: Aug. 18, 1998

(30) Foreign Application Priority Data

Aug. 21, 1997 (DE) .......................... 197 36 112

(51) Int. Cl.⁷ .................. A61K 7/043; A61K 31/56; A61K 31/785

(52) U.S. Cl. .................. 424/61; 424/78.05; 514/169

(58) Field of Search ................. 424/61, 78.05; 514/169

(56) References Cited

U.S. PATENT DOCUMENTS

| 3,861,932 A | | 1/1975 | Kabacoff et al. ............ 106/187 |
| 4,210,633 A | | 7/1980 | Takruri et al. .............. 424/80 |
| 4,250,164 A | * | 2/1981 | Bernstein ..................... 424/61 |
| 5,091,171 A | * | 2/1992 | Yu et al. ..................... 424/642 |
| 5,120,530 A | * | 6/1992 | Ferro et al. ................... 424/61 |
| 5,258,186 A | * | 11/1993 | Ohmura et al. ............. 424/497 |
| 5,264,206 A | * | 11/1993 | Bohn et al. .................. 424/61 |
| 5,275,807 A | * | 1/1994 | Pappas et al. ................ 424/61 |

FOREIGN PATENT DOCUMENTS

| DE | 2 423 849 | | 12/1974 |
| DE | 195 29 085 A1 | | 2/1997 |
| EP | 0 226 984 | | 12/1986 |
| EP | 0 226 984 A1 | | 7/1987 |
| EP | 0 515 312 A2 | | 11/1992 |
| GB | 2 188 844 A | | 10/1987 |
| WO | WO 87/02580 | | 5/1987 |
| WO | WO 95/03838 | | 2/1995 |
| WO | WO-96/14048 A | * | 5/1996 |
| WO | WO 96/36311 | * | 11/1996 |
| WO | WO 97/43644 | | 5/1997 |
| WO | WO 97/34644 | | 9/1997 |
| WO | WO-97/34644 A1 | * | 9/1997 |

OTHER PUBLICATIONS

Wilkinsin, et al., Eds., Harry's Cosmeticology, 7th Ed., Chemical Publishing, New York (1982), pp. 375–379 and 383–385.*

Derwent Abstract No. 85–021807 corresponding to JP 59–216822A.

* cited by examiner

*Primary Examiner*—Diana Dudash
*Assistant Examiner*—Alysia Berman
(74) *Attorney, Agent, or Firm*—Finnegan, Henderson, Farabow, Garrett & Dunner, LLP

(57) ABSTRACT

This invention relates to a nail polish comprising one or more glucocorticoids useful in treating nails which show changes due to the syndrome of psoriasis.

28 Claims, No Drawings

ANTIPSORIATIC NAIL POLISH

The involvement of the finger nails and toe nails in the psoriasis syndrome is widespread. According to literature references, up to 50% of all psoriasis patients also show changes to the nails in addition to the characteristic skin symptoms. The nail changes are found more frequently on the fingers than on the toes and are identified in the order of their frequency by the following symptoms:

Pitting (punctate or irregularly shaped depressions arranged on the surface of the body of the nail in a certain pattern or alternatively irregularly), discoloration of the nail bed, onycholysis (detachment of the body of the nail from the nail bed), subungual keratosis, or anomalies of the body of the nail.

For treatment of the nails affected by psoriasis, the following four methods were used until now, but without sweeping success, in addition to PUVA phototherapy:

One treatment method, the systemic method, consists in administering methotrexate, retinoids or cyclosporin A orally. This necessitates a long-term treatment, which according to experience can lead to intoxication.

Another method consists in injecting intralesional corticosteroids. This method is naturally very painful, so that the patients are only initially ready to cooperate initially, but later refuse treatment.

With a further method of surgically removing the affected nails, good treatment results can indeed be achieved, but intervention is only temporary because within one week after regeneration of the body of the nail psoriasis may return.

A fourth, gentler, method consists in treating the nails locally with specific, antipsoriatic substances such as dithranol, vitamin D analogs, or corticosteroids. In this context, all sorts of treatment methods have been attempted. Thus, in a combined treatment the nails are first treated with solutions of the antipsoriatic substances. Then cream dressings are applied at night. Even this treatment method is naturally very unpleasant and psychologically distressing for the patient. First, the treatment of the nails with solutions is necessary several times daily. Second, the treated nails must be covered with dressings at night.

This leads to the results that the treatment of patients, usually for many months, is often not completed. Patients become disheartened and negligent and thus no therapeutic result materializes. The success of treatment in this method is furthermore adversely affected because the solutions and creams are usually miscible with water or are hydrophilic and can therefore be removed from the nail surface or dissolved out of the nail by washing, bathing and showering and thus consequently then have to be reapplied again. As a result of this, the treatment with these topical agents is ineffective and, moreover, highly uneconomical.

High hopes have therefore been placed in another method, namely in the treatment of the affected nails with a 50:50 mixture of commercially available corticosteroid-containing lotions, creams or ointments with commercially available clear cosmetic varnishes (U.S. Pat. No. 4,250,164). This method, however, although already known for a long time, has not generally found its way into therapy since a satisfactory result from these—naturally physically unstable—mixtures do not appear, presumably for lack of sufficient bioavailability of the active compound from the solid system present after the drying of the mixture.

Therefore, many cases, in particular the severe cases, have been treated as before using the surgical method described above or using painful intralesional injections or using combined solution and cream therapy.

WO 97/43644 discloses a topical formulation suitable for the treatment of nail psoriasis comprising at least one glucocorticoid, at least one spreading solvent, at least one readily volatile solvent and a film-forming agent. This topical formulation has the disadvantage that a spreading solvent is necessary. This additional spreading solvent increases the price of the formulation and since It is not clear if this spreading solvent is physiologically acceptable, the approval of the formulation becomes more complicated or even impossible.

The invention aims to make available a glucocorticoid-containing formulation which does not have the disadvantages described above or only has them to a minor extent. In particular, the formulation should guarantee a good penetration of the nail by the glucocorticoid and thus a good bioavailability though a water-insoluble film-forming agent is used.

The invention further aims to make available a glucocorticoid formulation, which does guarantee a good penetration of the nail by the glucocorticoid and thus a good bioavailability, comprising no additional spreading or penetration promoting solvent or substance.

The object is achieved by the nail polish according to the invention, comprising one or more glucocorticoids, a physiologically tolerable, preferably readily volatile, solvent or solvent mixture and one or more water-insoluble film-forming agents.

Antipsoriatic glucocorticoids are, for example: alclometasone dipropionate, amcinonide, beclomethasone dipropionate, bendacort, betamethasone benzoate, betamethasone dipropionate, betamethasone valerate, budesonide, chlorquinaldol, clioquinol, clobetasol propionate, clobetasone butyrate, desonide, desoximetasone, dexamethasone, dichlorisone, difiorasone diacetate, diflucortolone valerate, difluprednate, fluazacort, flucinolone acetonide, fluclorolone acetonide, fludroxycortide, flumethasone pivalate, fluocinolone acetonide, fluocinonide, fluocortolone, fluorometholone, flupamesone, fluprednidene, fluprednidene acetate, flurandrenolide, halcinonide, halometasone, hydrocortamate, hydrocortisone butyrate, methylprednisolone aceponate, mometasone furoate, prednicarbate, prednisolone, prednisone, tixocortol, triamcinolone acetonide.

The glucocorticosteroids can be present either as free alcohols or in the form of their esters.

Suitable water-insoluble film-forming agents are, for example, cellulose derivatives such as cellulose nitrate or ethylcellulose or physiologically acceptable polymers such as are customary, for example, in cosmetics. Mention may be made, for example, of poly(vinyl acetate), and partially hydrolyzed poly(vinyl acetate); copolymers of vinyl acetate with acrylic acid or crotonic acid or monoalkyl maleate; ternary copolymers of vinyl acetate with crotonic acid and vinyl neodecanoate, or crotonic acid and vinyl propionate; copolymers of methyl vinyl ether and monoalkyl maleates, and in particular monobutyl maleate; copolymers of fatty acid vinyl esters and acrylic acid or methacrylic acid; copolymers of N-vinylpyrrolidone, methacrylic acid and alkyl methacrylates; copolymers of acrylic acid and methacrylic acid or alkyl acrylates or alkyl methacrylates, in particular containing quaternary ammonium groups; or polymers, copolymers or mixtures comprising ethyl acrylate, methyl methacry ate or trimethylammonioethyl methacrylate chloride or polyvinyl acetals and polyvinyl butyrals, alkyl-substituted poly-N-vinylpyrrolidone, alkyl esters of copolymers of olefins and maleic anhydride, reaction products of colophony with acrylic acid and also benzoins. In the esters, the alkyl radicals are usually short-chain and mostly do not have more than four carbon atoms.

Suitable physiologically tolerable solvents are substances such as hydrocarbons, halogenated hydrocarbons, alcohols, ethers, ketones and esters which are customary in cosmetics, in particular acetate esters of monohydric alcohols such as ethyl acetate and butyl acetate, optionally as a mixture with aromatic hydrocarbons such as toluene and/or alcohols such as ethanol or isopropanol.

As is known, the combination of the solvents is of crucial importance for the drying time, spreading ability, and other important properties of the varnish or of the varnish film. The solvent system preferably consists of an optimal mixture of low-boiling components (solvents having a boiling point up to 100° C.) and medium-boiling components (solvents having a boiling point up to 150° C.), optionally with a small proportion of high-boiling components (solvents having a boiling point up to 200° C.).

Readily volatile solvents are understood as meaning compounds which have a boiling point which is below 80° C.

The nail polishes according to the invention can further contain additives customary in cosmetics, such as plasticizers based on phthalate or camphor, colorants or color pigments, pearl luster agents, sedimentation retardants, sulfonamide resins, silicates, aromatic substances, lanolin derivatives, sunscreens such as 2-hydroxy-4-methoxybenzophenone, antimicrobial substances, and substances having keratolytic and/or keratoplastic action, such as ammonium sulfite, esters and salts of thioglycolic acid, urea, allantoin, enzymes, and salicylic acid.

Using the nail polish according to the invention, one can achieve a drastic cure in the treatment of psoriatic nails, the nail usually growing again without deformation. In view of the poor therapeutic experiences until now, this is an extremely important finding.

The nail polish according to the invention is also suitable for prophylactic use against psoriatic nails, a sufficiently high active compound depot being achieved in the nail such that a possible recurrence does not break out.

The content of active compound in the nail polish according to the invention is dependent on the structure of each active compound and thus on its release from the varnish film, its penetration behavior in the nail, and its potency.

In the nail polish according to the invention, (i.e., the solvent-containing use form) the active compound is in general contained in an amount from 0.5 to 20, preferably 2 to 15, percent by weight. The minimum content of active compound in the medicinal nail polishes (i.e., those for treatment) is preferably 8 percent by weight; the nail polishes used for prophylaxis preferably contain 1 to 4 percent by weight of active compound.

Colored or pigmented nail polishes have the-advantage, for example, that the preparation according to the invention can be tailored to the esthetic perception of the patient.

The nail polish is prepared in a customary manner by mixing together the individual components and—if necessary—further processing tailored to the respective preparation.

The nail polish according to the invention has the following composition:

EXAMPLE 1

| | |
|---|---|
| Clobetasol-17-propionate | 8.0% |
| 50% strength solution of a copolymer of methyl vinyl ether and monobutyl maleate in isopropyl alcohol | 30.0% |
| Isopropyl alcohol | 31.0% |
| Ethyl acetate | 31.0% |

The percentage quantitative data are by weight.
The nail polish is prepared by dissolving the various components in the solvents.

EXAMPLE 2

| | |
|---|---|
| Desoximetasone | 5.0% |
| Ethyl acrylate/methyl methacrylate/trimethylammonioethyl methacrylate chloride in a molar ratio of 1:2:0.2 (EUDRAGIT ® RL 100) | 12.0% |
| Ethanol 96% | 60.0% |
| Ethyl acetate | 13.0% |
| Butyl acetate | 10.0% |

EXAMPLE 3

| | |
|---|---|
| Betamethasone dipropionate | 5.0% |
| Ethylcellulose | 11.0% |
| Ethyl acetate | 30.0% |
| Butyl acetate | 34.0% |
| Ethanol 96% | 20.0% |

EXAMPLE 4

| | |
|---|---|
| Prednicarbate | 7.5% |
| Polyvinyl butyral | 4.7% |
| Cellulose nitrate | 4.3% |
| Dibutyl phthalate | 0.6% |
| Ethyl acetate | 10.0% |
| Ethanol 96% | 72.9% |

EXAMPLE 5

| | |
|---|---|
| Halcinonide | 2.0% |
| Methacrylic acid/ethyl acrylate 1:1 copolymer | 6.5% |
| Ethanol 96% | 71.5% |
| Ethyl acetate | 20.0% |

The action of the nail polish according to the invention is demonstrated in permeation tests on cowhorn platelets and in treatment experiments on subjects. The permeation test on cowhorn platelets allows the release of an active compound from a certain preparation and the subsequent permeation through keratin material to be tested.

At present, there are still no topical preparations known for the treatment of nail psoriasis with glucocorticoids from which the active compound is released in sufficient amount, then penetrates into the nails and can thus act in a therapeutic dose on the underlying matrix or the nail bed.

As a control example, the following was used:

| | |
|---|---|
| clobetasol-17-propionate in isopropyl alcohol | 8.0% is dissolved 92.0%. |

A) Permeation Test on Cowhorn Platelets

The measurement of the active compound permeation is carried out by means of time-resolved ATR technique (time-resolved infrared attenuated total reflection—see Th. M. Bayerl et al.; J. Invest. Dermatol. 105:291–295, 1995):

100 µl of the test preparation (test preparation or control example) are applied to a defined area on the top of a cowhorn platelet of 0.5 mm thickness. After a drying time of 15 minutes, the cowhorn platelet with the varnish layer was applied to the measuring crystal and pressed on by an external device. The contact pressure and the penetration depth of the measuring beam were selected here such that the IR spectrum did not record any portions of the cowhorn platelet. Spectra of the varnish layer were recorded for 48 hours and the decrease in the active compound bands which is to be attributed to the penetration of the active compound into the keratin material was investigated.

It is seen here that the characteristic band of clobetasol-17-propionate at 1660 cm$^{-1}$ decreases to approximately 60% of the starting value in the clear varnish film of the nail polish according to the invention in the measurement period of 48 hours, while the active compound precipitates almost quantitatively from the control example on evaporating the solvent and is thus no longer available for penetration into the keratin material.

Moreover, it was possible to detect clobetasol-17-propionate qualitatively on the back of the cowhorn platelet employed after the application of the nail polish according to the invention, while after the application of the control preparation it was not possible to produce this detection.

Although in EP 0 226 984 similar penetration properties of certain antimycotic hydroxypyridone compounds from solid varnish films are described, this is nevertheless a surprising finding, since it was not to be foreseen that glucocorticoids, which constitute a bulky, rigid cyclopentanoperhydrophenanthrene four-ring system, are more bioavailable from the water-insoluble solid system present after the drying of the varnish preparation and permeate into or through the keratin material better than from the isopropanolic solution.

B) Activity Testing

1) The antipsoriatic properties of the nail polish according to the invention have been tested on 2 people with long-standing two-handed thumb nail psoriasis. A daily treatment of the affected nails for only four months with the nail polish according to the invention according to Example 1 led to the growing out of symptom-free new nail plates.

2) The antipsoriatic properties of the nail polish according to the invention have been tested on 14 people with nail psoriasis. A treatment two times a week of the affected nails for only six months with the nail polish according to the invention according to Example 1 led to a lasting improvement of the nail plates or to the growing out of symptom free new nail plates in 86% of the cases (12 people out of 14).

We claim:

1. A nail polish for treating psoriasis of the nail, comprising one or more glucocorticoids, one or more physiologically tolerable solvents, and one or more water-insoluble film-forming agents comprising one or more quaternary ammonium groups to form a stable nail polish.

2. A nail polish according to claim 1, which comprises a glucocorticoid selected from the group consisting of alclometasone dipropionate, amcinonide, beclomethasone dipropionate, bendacort, betamethasone benzoate, betamethasone dipropionate, betamethasone valerate, budesonide, chlorquinaldol, clioquinol, clobetasol propionate, clobetasone butyrate, desonide, desoximetasone, dexamethasone, dichlorisone, diflorasone diacetate, diflucortolone valerate, difluprednate, fluazacort, flucinolone acetonide, fluclorolone acetonide, fludroxycortide, flumethasone pivalate, fluocinolone acetonide, fluocinonide, fluocortolone, fluorometholone, flupamesone, fluprednidene, fluprednidene acetate, flurandrenolide, halcinonide, halometasone, hydrocortamate, hydrocortisone butyrate, methylprednisolone aceponate, mometasone furoate, prednicarbate, prednisolone, prednisone, tixocortol, triamcinolone acetonide, and a mixture thereof.

3. A nail polish according to claim 1, which comprises a glucocorticoid selected from the group consisting of clobetasol propionate, desoximetasone, betamethasone dipropionate, prednicarbate and halcinonide.

4. A nail polish according to claim 1, comprising between about 0.5% to about 20% by weight one or more glucocorticoids.

5. A nail polish according to claim 1, comprising between about 2% to about 15% by weight one or more glucocorticoids.

6. A nail polish according to claim 1, where the glucocorticoids are in the form of free alcohols or esters.

7. A nail polish according to claim 1, wherein the content of glucocorticoid is at least 8% by weight.

8. A nail polish according to claim 1 wherein the glucocorticoid is present in the amount of about 1% to about 4% by weight.

9. A nail polish according to claim 1, which further comprises a cellulose derivative as another water-insoluble film-forming agent.

10. A nail polish according to claim 9, which further comprises cellulose nitrate, ethylcellulose, or mixtures thereof as another water-insoluble film-forming agent.

11. A nail polish according to claim 1, which further comprises a poly(vinyl acetate), partially hydrolyzed poly (vinyl acetate); copolymers of vinyl acetate with acrylic acid, or crotonic acid or monoalkyl maleate; ternary polymers of vinyl acetate with crotonic acids and vinyl neodecanoate; ternary polymers of vinyl acetate with crotonic acid and vinyl propionate; copolymers methyl ethyl vinyl ether and monoalkyl maleates; copolymers of fatty acid vinyl esters and acrylic acid or methacrylic acid; copolymers of N-vinylpyrrolidone, methacrylic acid, and alkyl methacrylates; copolymers of acrylic acid and methacrylic acid, alkyl acrylates, or alkyl methacylates as another water-insoluble film-forming agent.

12. A nail polish according to claim 11, where said other water-insoluble film-forming agent is a copolymer of methyl vinyl ether and monobutyl maleate.

13. A nail polish according to claim 1, which further comprises a polymer, copolymer, or mixture comprising one or more of ethyl acrylate, methyl methacrylate, trimethylammonioethyl methacrylate chloride, polyvinyl acetals, polyvinyl butyrals, alkyl-substituted poly-N-vinylpyrrolidone, alkyl esters of copolymers of olefins and maleic anhydride, reaction products of colophony with acrylic acid, and benzoins as another water-insoluble film-forming agent.

14. A nail polish according to claim 1 where the water-insoluble film-forming agent comprises ethyl acrylate, methyl methacrylate, and trimethylammonioethyl methacrylate chloride in a molar ratio of 1:2:0.2.

15. A nail polish according to claim 1, where the physiologically tolerable solvent is selected from the group consisting of hydrocarbons, halogenated hydrocarbons, alcohols, ethers, ketones, esters, and mixtures thereof.

16. A nail polish according to claim 15, where the physiologically tolerable solvent comprises acetate esters of monohydric alcohols.

17. A nail polish according to claim 1, where the physiologically tolerable solvent is selected from the group consisting of ethyl acetate, butyl acetate, mixtures thereof, mixtures with aromatic hydrocarbons, and mixtures with alcohols.

18. A nail polish according to claim 17 where the aromatic hydrocarbon is toluene.

19. A nail polish according to claim 17 where the alcohol is selected from the group consisting of ethanol, isopropanol, and a mixture thereof.

20. A nail polish according to claim 1, further comprising a phthalate-based plasticizer, a camphor-based plasticizer, a colorant or color pigment, pearl luster agents, sedimentation retardants, sulfonamide resins, silicates, aromatic substances, lanolin derivatives, sunscreens, antimicrobial substances, substances having keratolytic activity, keratoplastic activity, or both, or mixtures thereof.

21. A nail polish according to claim 20, where the additive sunscreen is 2-hydroxy-4-methoxybenzophenone.

22. A nail polish according to claim 20, where the keratolytic active substance, the keratoplastic active substance, or both is ammonium sulfite, esters and salts of thioglycolic acid, urea, allantoin, enzymes, salicylic acid, or mixtures thereof.

23. A method of treating psoriasis of the nail, comprising applying an effective amount of one or more glucocorticoids to a nail in need of said treatment, together with one or more physiologically tolerable solvents and one or more water-insoluble film-forming agents.

24. A nail polish according to claim 1 for treating psoriasis of the nail, wherein the nail polish is substantially free of water.

25. A nail polish according to claim 24 for treating psoriasis of the nail, wherein the nail polish contains less than about 3% water by weight.

26. A nail polish according to claim 1 for treating psoriasis of the nail, wherein said one or more glucocorticoids is present in at least about 0.5% by weight.

27. A method for treating psoriasis of nails, comprising applying an effective amount of a nail polish according to claim 1 to a nail of a host.

28. A nail polish of claim 1, wherein said water-insoluble film-forming agent comprising one or more quaternary ammonium groups comprises a copolymer of fatty acid vinyl esters and acrylic acid or methacrylates; or a copolymer of acrylic acid and methacrylic acid, alkyl acrylates, or alkyl methacylates.

\* \* \* \* \*

UNITED STATES PATENT AND TRADEMARK OFFICE
CERTIFICATE OF CORRECTION

PATENT NO. : 6,352,686 B2  
DATED : March 5, 2002  
INVENTOR(S) : Bohn et al.

It is certified that error appears in the above-identified patent and that said Letters Patent is hereby corrected as shown below:

Column 6,  
Line 28, "prednicarbate and" should read -- prednicarbate, and --.  
Line 59, "methacylates" should read -- methacrylates --.

Column 8,  
Line 30, "methacylates" should read -- methacrylates --.

Signed and Sealed this

Twenty-ninth Day of October, 2002

Attest:

Attesting Officer

JAMES E. ROGAN  
*Director of the United States Patent and Trademark Office*